United States Patent [19]

Ohno et al.

[11] 4,017,598
[45] Apr. 12, 1977

[54] PREPARATION OF READILY DISINTEGRABLE TABLETS

[75] Inventors: Shigeru Ohno, Kamakura; Noboru Hoshi, Higashikurume; Fujio Sekigawa, Yono, all of Japan

[73] Assignee: Shin-Etsu Chemical Company Limited, Tokyo, Japan

[22] Filed: Apr. 22, 1975

[21] Appl. No.: 570,959

[30] Foreign Application Priority Data

Apr. 27, 1974 Japan .............................. 49-47875

[52] U.S. Cl. .................................. 424/35; 424/362
[51] Int. Cl.² .................... A61J 3/10; A61K 47/00
[58] Field of Search ............................. 424/362, 35

[56] References Cited

UNITED STATES PATENTS

| | | | |
|---|---|---|---|
| 2,883,327 | 4/1959 | Dale | 424/362 X |
| 3,065,143 | 11/1962 | Christensen et al. | 424/35 X |
| 3,079,303 | 2/1963 | Raff et al. | 424/362 X |
| 3,133,863 | 5/1964 | Tansey | 424/22 X |
| 3,266,992 | 8/1966 | De Jong | 424/362 X |
| 3,725,556 | 4/1973 | Hanssen | 424/362 X |
| 3,852,421 | 12/1974 | Koyanagi et al. | 424/362 X |
| 3,907,983 | 9/1975 | Seth | 424/35 |
| R27,679 | 6/1973 | Bentholm et al. | 424/362 X |

OTHER PUBLICATIONS

Khan et al., Chem. Abst. 82, No. 116041M, (1975), Abst. of J. Pharm, Sci. 64(1): 166–168 (1975).
Mendel, Chem. Abst. 82, No. 129227b, (1975), Abst. of Pharm. Acta. Helv. 49(7/8): 248–250 (1974). .
Khan et al., Chem. Abst. 82, No. 144889N, (1975), Abst. of J. Pharm. Pharmacol. 26, Suppl. 106p–107p(1974).

*Primary Examiner*—Shep K. Rose
*Attorney, Agent, or Firm*—Toren, McGeady and Stanger

[57] ABSTRACT

Methylcellulose with or without the addition of medically active ingredients and other additives is first granulated by a known method into granules of appropriate size and then the granules are blended with a disintegrator and compressed into tablets. The tablets obtained by the method have sufficient hardness and very short disintegration time when taken into the human body in comparison with the poor disintegrability of tablets directly shaped from powdery methylcellulose or a methylcellulose-based mixture of active ingredients. The method is useful for tableting some medicinals of poor tabletability, such as, pancreatin which require large amounts of a binder to be successfully shaped into tablets. Tablets of methylcellulose prepared in accordance with the method can find use as a non-caloried food.

9 Claims, No Drawings

PREPARATION OF READILY DISINTEGRABLE TABLETS

FIELD OF THE INVENTION

This invention relates to a novel method for the preparation of readily-disintegrable pharmaceutical tablets.

DESCRIPTION OF THE PRIOR ART

Methylcellulose is widely employed in the preparation of various kinds of tablets as a binder for the main ingredients (see, for example, L. Lachman et al., editors, The Theory and Practice of Industrial Pharmacy, Lea & Febiger, Philadelphia, 1970, p. 312 et seq.). In the preparation of such tablets, methylcellulose is formulated normally in an amount of a few percent, or 10 percent at the most, by weight based on the main ingredients and if the amount is too large amount of it results in the decreased disintegrability of the tablets when taken into the human body. Therefore, methylcellulose cannot be employed practically when an increased amount of a binder is required for the preparation of tablets comprising an active ingredient which is difficult to shape into tablets because of the low cohesive ingredients.

On the other hand, methylcellulose itself is excellent as a non-nutritious edible capable of giving the sensation of full stomach when taken in the form of tablets. Tablets shaped from methylcellulose of ordinary grade, however, hardly disintegrate in the stomach after administration and, consequently, fail to give the feeling of a full stomach by disintegrating and swelling in the stomach.

OBJECT OF THE INVENTION

It is therefore an object of this invention to provide a method free of the above difficulties for preparing methylcellulose-containing tablets that are sufficiently hard but are readily-disintegrable in the stomach.

SUMMARY OF THE INVENTION

The present invention is a method for the preparation of readily-disintegrable tablets characterized in that granules made from a water-soluble methylcellulose or a mixture of a water-soluble methylcellulose and medically active ingredients are admixed with a disintegrator and then shaped into tablets.

DETAILED DESCRIPTION OF THE INVENTION

The invention is based on the discovery that tablets with unexpectedly good disintegrability can be obtained with methylcellulose as the main ingredient when the methylcellulose is formed into granules in advance by a known method and the granules of methylcellulose are admixed with a disintegrator and are shaped into tablets.

To further describe the method, tablets which are the objective of the present invention include both those of methylcellulose as the sole ingredient and those of methylcellulose admixed with medically active ingredients amd other additives. In both cases, the methylcellulose or the mixture of methylcellulose with other additives, e.g., medically active ingredients, are required to be granulated in advance.

Granules of methylcellulose or methylcellulose-based mixture are prepared by several methods, such as, the granulation of the methylcellulose (or the methylcellulose-based mixture) wetted with a suitable liquid and kneaded or granulation in a fluidized bed. In the former method, the methylcellulose or the mixture of methylcellulose with other ingredients is moistened with a wetting liquid of water or an alcohol, such as, methanol, ethanol and isopropanol either alone or in combination, and kneaded in a kneader followed by granulation by a known method, such as, extrusion granulation and oscillation granulation.

The wetting liquid employed as above is preferably a mixed solvent of water and an alcohol in a ratio of from 9:1 to 1:9, or preferably from 7:3 to 3:7. When the ratio of water in the mixed solvent is too large, the increased stickiness of the wet mass randers the granulation process very difficult while a smaller ratio of water also brings about some difficulties in the granulation process because of the insufficient cohesion of the wet mass. The amount of the mixed solvent of water and an alcohol to be employed is determined by several factors, such as, the grade and particle size of the methylcellulose, kind of the medically active ingredients to be admixed with the methylcellulose, the size of the granules to be obtained and the method of granulation, and thus cannot be stated definitely given. It is generally advisable, however, that from 20 to 80 parts by weight of the mixed solvent of water and an alcohol be employed for 100 parts by weight of the methylcellulose powder or a mixture of the methylcellulose powder with other ingredients.

In the alternative method of granulation, granules can be prepared in a fluidized bed as is mentioned above. As the spraying liquid employed in the method, water, methanol, ethanol or isopropanol are employed either alone or in combination. Usually a mixed solvent of water and an alcohol is suitable for the purpose and the mixing ratio of water to alcohol is from 9:1 to 2:8, or preferably from 9:1 to 3:7. When the content of water is too high in the spraying liquid, the distribution in the size of the resulting granules will become too broad although a savings in time can be realized for the completion of the granulation. However, some difficulties can be encountered in the granulation procedure with too low a content of water in the spraying liquid. The operation of granulation in a fluidized bed is conducted until granules of desired size are formed and the amount of the spraying liquid consumed during the granulation process is in the range of from 5 to 50 parts by weight per 100 parts by weight of the powdery material to be granulated.

The size of the granules to be shaped into tablets is determined according to the method described in the United States Pharmacopoeia, 18th revision, "Testing for Powder Fineness" and it is desirable that the size of the granules is such that all of the granules pass through the No. 10 sieve (U.S. Standard, 2,000 $\mu$m opening) and less than 5% of them pass through the No. 80 sieve (U.S. Standard, 177 $\mu$m opening). Larger granule size leads toward nonuniformity in the weight of the individual tablets obtained by tableting the granules and a smaller granule size causes inferior disintegrability of the resulting tablets.

It is optional in the present method that various kinds of additives are added before granulation to the methylcellulose or the mixture of methylcellulose and medically active ingredients.

The methylcellulose suitable for the method of the present invention may be a conventional water-soluble type commercially available, but it is advisable that the methoxy content of the methylcellulose be in the range of from 20% to 32% by weight corresponding to a degree of substitution of from 1.2 to 2.0 and a viscosity of a 2% by weight aqueous solution in the range of from 5 to 10,000 centipoise, and preferably, from 100 to 8,000 centipoise, at 20° C.

The granules to be shaped into tablets according to the method of the present invention may be granulated from a powdery mixture of methylcellulose and medically active ingredients as is mentioned above and the medically active ingredients may be in the form of either powder or liquid. It is when rapid disintegration of the tablets containing the medically active ingredients are desired on the arrival of the tablets at an appropriate part of the alimentary tract that the admixed medically active ingredient is in powder form as is the case in pancreatin which is one of the medicinals most difficult to shape into tablets due low cohesiveness. The amount of the powdery medical ingredient to be admixed with the methylcellulose is in the range up to 300% by weight based on the weight of the methylcellulose. When the medically active ingredient is difficult to take because of objectionable taste or odor as is the case of castor oil, the admixed medically active ingredient would be in liquid form. Such a liquid ingredient is mixed with the methylcellulose in an amount of up to 50% by weight based on the weight of the methylcellulose.

According to the method of the present invention, the granules obtained as above and composed of methylcellulose or a mixture of methylcellulose with a medically active ingredient is admixed with a disintegrator and then shaped into tablets by a known method. Disintegrators suitable for the purpose are exemplified by microcrystalline cellulose, the calcium salt of carboxymethylcellulose and several kinds of cellulose ethers with a low degree of substitution which swell but hardly dissolve in water, such as, hydroxypropylcellulose with from 0.1 to 1.2 of molar substitution, methylcellulose with from 0.1 to 1.2, of substitution, and hydroxypropylmethylcellulose with from 0.1 to 1.2, of molar substitution for methoxy groups and hydroxypropoxy groups.

The amount of the disintegrator to be admixed should be determined in accordance with various factors, such as, the kind of the disintegrator, the size of the granules and the desired disintegrability. Generally the disintegrator is blended with the granules in an amount of from 3% to 200% by weight, or preferably, from 10% to 100% by weight, based on the weight of the granules. Too small an amount of the disintegrator results in an insufficient disintegrability of the resultant tablets and too large an amount of the disintegrator cannot give tablets with a satisfactory mechanical strength due to the lack in the binding force. There is also the disadvantage that the dose of the tablets to be administrated must be increased because of the decreased ratio of the granules i.e., decreased content of the methylcellulose or the medically active ingredient in the finished tablets.

It is optional in the method of the present invention to add, in combination with the disintegrator as described above, small amounts of various kinds of additives including several medically active ingredients, lubricants, such as, talc and calcium stearate, coloring agents, such as, edible dyes and aluminum lake pigments, sweetenings, such as, sucrose and fructose and flavorings, such as, vanilla essence and menthol.

The method of tableting is not limiting and any type of tablet machine can be used including a single-punch tablet machine and a rotary tablet machine.

In the following examples illustrating the method of the present invention, parts are all in parts by weight and the grades of the methylcellulose employed and the procedure for granulation of the methylcellulose were as described below.

Methylcellulose A (powder): grade SM-4000, a product of Shin-Etsu Chemical Co., Japan, having a methoxy content of 29.2% by weight corresponding to a degree of substitution of 1.75. The particle size distribution of the methylcellulose was such that all of it passed through a No. 40 sieve (U.S. Standard, 420 $\mu$m opening) but 8.5% of it remained on a No. 80 sieve (177 $\mu$m opening). The viscosity of the 2% by weight aqueous solution was 4,350 centipoise at 20° C.

Methylcellulose B (powder): grade SM-1500, a product of Shin-Etsu Chemical Co., Japan, having a methoxy content of 28.8% by weight corresponding to a degree of substitution of 1.72. The particle size distribution was such that all of it passed through a No. 40 sieve, but 6.5% of it remained on a No. 80 sieve. The viscosity of the 2% by weight aqueous solution of it was 1,670 centipoise at 20° C.

Preparation of granules of the methylcellulose A and B: 1,000 parts of the methylcellulose to be granulated was moistened with 400 parts of a mixed solvent of water and ethanol (5:5 by weight) and kneaded in a Henschel mixer. The methylcellulose thus moistened and kneaded was then granulated in an extrusion granulator with a screen of 0.6 mm opening and dried in an air-circulation dryer for 5 hours at 60° C followed by the removal of coarser granules by passing through a U.S. Standard No. 10 sieve with an opening of 2,000 $\mu$m.

EXAMPLE 1

Four kinds of formulations as shown in Table 1 below were subjected to tableting by use of a rotary tablet machine into flat face tablets of 13 mm diameter weighing 500 mg each and having a hardness ranging from 6 to 7 kg by a Monsanto Hardness Tester. The disintegration time of these tablets was determined in accordance with the method described in The United States Pharmacopoeia, 18th revision, "Disintegration Test for Uncoated Tablets" to give the results shown in the table. It is obvious from the results that the disintegration of the tablets prepared in accordance with the method of the present invention is very rapid.

Table 1

| Formulation No. | Control | | | Present invention |
|---|---|---|---|---|
| | 1 | 2 | 3 | 4 |
| Methylcellulose A (powder), parts | 1,000 | 700 | — | — |
| Methylcellulose A (granules), parts | — | — | 1,000 | 700 |
| Microcrystalline cellulose (*), parts | — | 300 | — | 300 |
| Calcium stearate, parts | 3 | 3 | 3 | 3 |
| Disintegration test | Not complete in 30 minutes | | | Complete in 30 to 40 seconds |

(*) Avicel, tradename by Asahi Chem. Ind. Co., Japan

EXAMPLE 2

In a control test (Formulation No. 5), a mixture of 500 parts of pancreatin, 300 parts of powdery methylcellulose A, 200 parts of the same microcrystalline cellulose as in the preceding example and 3 parts of calcium stearate was directly subjected to tableting by use of a rotary tablet machine into tablets of 9 mm diameter weighing 280 mg each and having a hardness of 2 to 3 kg by Monsanto Hardness Tester. The disintegration test gave a result that disintegration was not complete in 30 minutes.

A test in accordance with the method of the present invention (Formulation No. 6) was undertaken in parallel with the control test above, in which 500 parts of pancreatin and 300 parts of the same methylcellulose powder were charged into a Henschel mixer together with 400 parts of a mixed solvent of isopropanol-water (6:4 by weight) and the kneaded mixture was granulated by use of an extrusion granulator with a screen of 0.6 mm opening into granules. The granules were dried in an air-circulation dryer for 5 hours at 60° C followed by the removal of coarser granules with a No. 10 U.S. Standard sieve. The granules were further blended with 200 parts of the microcrystalline cellulose and 3 parts of calcium stearate and the blend was subjected to tableting as in the control test into tablets of the same size and weight having a hardness of 4 to 5 kg. The disintegration time measured for these tablets was in the range of from 5 minutes and 10 seconds to 7 minutes and 20 seconds.

As is shown above, it is possible to prepare tablets containing a substantial amount of pancreatin and having sufficient hardness and a very short disintegration time despite the generally accepted difficulty in the preparation of tablets containing pancreatin due to its very low tabletability.

EXAMPLE 3 (FORMULATION NO. 7)

The granules of methylcellulose A in an amount of 700 parts were admixed with 300 parts of hydroxypropylcellulose with a low degree of substitution containing 12.1 % by weight of hydroxypropoxy groups corresponding to a molar substitution of 0.29, which had been moistened with 5 parts of an ethanolic solution of 0.2 part of menthol and then air-dried, 30 parts of fructose, 3 parts of magnesium stearate, 0.4 part of tartrazine aluminum lake and 0.04 part of Brilliant Blue FCF aluminum lake and the mixture was subjected to tableting by use of a rotary tablet machine into tablets of 13 mm diameter weighing 500 mg each. The hardness of the tablets was 6 to 7 kg by Monsanto Hardness Tester and the disintegration time of the tablets as measured in Example 1 was 30 to 40 seconds.

EXAMPLE 4 (FORMULATION NO. 8)

Powdery methylcellulose B in an amount of 300 parts was blended and kneaded in a Henschel mixer with 200 parts of powdered ginseng, 200 parts of powdered garlic, 100 parts of powdered licorice and 100 parts of powdered cinnamon by moistening with 350 parts of water-ethanol (4:6 by weight) mixed solvent and granules were obtained from the above blend by use of an extrusion granulator with a screen of 0.6 mm opening followed by drying in an air-circulation dryer for 5 hours at 60° C and removal of coarser granules by passing through a No. 10 U.S. Standard sieve.

The granules thus obtained were further blended with 100 parts of calcium salt of carboxymethylcellulose and 5 parts of magnesium stearate and subjected to tableting by use of a rotary tablet machine into tablets of 9 mm diameter weighing 250 mg each. The hardness of the tablets was 4 to 5 kg by Monsanto Hardness Tester and the disintegration time of the tablets measured as in Example 1 was from 1 minute and 20 seconds to 1 minute and 40 seconds.

EXAMPLE 5 (FORMULATION NO. 9)

Powdery methylcellulose A in an amount of 5 kg was charged into a fluidizing granulator of Model WSG-5 made by Firma Werner Glatt, West Germany, and the machine was operated for 15 minutes during which a mixed solvent of water-ethanol (6:4 by weight) was sprayed at a rate of 100 ml/minute to give granules of the methylcellulose following by the removal of coarser granules by passing through a No. 10 U.S. Standard sieve.

The blend of 1,000 parts of the above granules with 3 parts of calcium stearate and 800 parts of methylcellulose with a low degree of substitution containing 14.4% by weight of methoxy groups corresponding to the degree of substitution 0.80 was subjected to tableting by use of a rotary tablet machine, into tablets of 13 mm diameter weighing 500 mg each. The hardness of the tablets was 6 to 7 kg by Monsanto Hardness Tester and the disintegration time of the tablets as measured as in Example 1 was 20 to 30 seconds in which disintegration was complete.

What is claimed is:

1. A method for the preparation of readily disintegrable tablets which comprises the steps of (a) granulating powdery methylcellulose wetted with a mixed solvent of water and and an alcohol selected from the group consisting of methanol, ethanol and propanol in a ratio of from 9:1 to 1:9 by weight into granules, (b) admixing a disintegrator selected from the group consisting of a microcrystalline cellulose, calcium salt of carboxymethylcellulose, methylcellulose with the degree of substitution in the range of from 0.1 to 1.2, hydroxypropylcellulose with the molar substitution in the range of from 0.1 to 1.2 and hydroxypropylmethylcellulose with the degree of molar substitution for the methoxy groups and hydroxypropoxy groups in the range of from 0.1 to 1.2 with said granules in an amount of from 3% to 200% by weight based on said granules to form a blend, and (c) shaping said blend into tablets.

2. The method as claimed in claim 1, wherein said mixed solvent is employed in an amount of from 20% to 80% by weight based on the weight of said powdery methylcellulose.

3. A method for the preparation of readily disintegrable tablets which comprises the steps of (a) granulating a material selected from the group consisting of powdery methylcellulose and mixtures of methylcellulose with medically active ingredients wetted with a mixed solvent of water and an alcohol selected from the group consisting of methanol, ethanol and propanol in a ratio of from 9:1 to 1:9 by weight into granules, (b) admixing a disintegrator selected from the group consisting of a microcrystalline cellulose, calcium salt of carboxymethylcellulose, methylcellulose with the degree of substitution in the range of from 0.1 to 1.2, hydroxypropylcellulose with the molar substitution in the range of from 0.1 to 1.2 and hydroxypropylmethylcellulose with the degree of molar substitution for the methoxy groups and hydroxypropoxy groups in the range of from 0.1 to 1.2 with said granules in an amount of from 3% to 200% by weight based on said granules to form a blend, and (c) shaping said blend into tablets.

4. The method as claimed in claim 3, wherein said mixed solvent is employed in an amount of from 20% to 80% by weight based on the weight of said powdery methylcellulose or said mixed powder of methylcellulose and a medically active ingredient.

5. The method as claimed in claim 1, wherein the size of said granules is such that all of said granules pass through a sieve with an opening of 2,000 µm and less than 5% by weight of said granules pass through a sieve with an opening of 177 µm.

6. The method as claimed in claim 1, wherein said methylcellulose has a content of the methoxy groups in the range of from 20% to 32% by weight.

7. The method as claimed in claim 1, wherein the viscosity of the 2% by weight aqueous solution of said methylcellulose is in the range of from 5 centipoise to 10,000 centipoise at 20° C.

8. The method as claimed in claim 3, wherein said mixed powder of methylcellulose and a medically active ingredient is a mixture of less than 300 parts by weight of said medically active ingredient and 100 parts by weight of said methylcellulose when said medically active ingredient is in powder form.

9. The method as claimed in claim 3, wherein said mixed powder of methylcellulose and a medically active ingredient is a mixture of less than 50 parts by weight of said medically active ingredient and 100 parts by weight of said methylcellulose when said medically active ingredient is in liquid form.

* * * * *